United States Patent [19]

Carroll et al.

[11] 4,405,814

[45] Sep. 20, 1983

[54] HYDROFORMYLATION OF FORMALDEHYDE WITH RHODIUM CATALYSTS

[75] Inventors: W. Eamon Carroll, Creve Coeur; Albert S. Chan, St. Charles, both of Mo.

[73] Assignee: Monsanto Company, St. Louis, Mo.

[21] Appl. No.: 290,622

[22] Filed: Aug. 5, 1981

[51] Int. Cl.³ .............................................. C07C 45/49
[52] U.S. Cl. .................................... 568/462; 568/458
[58] Field of Search ................................ 568/462, 458

[56] References Cited

U.S. PATENT DOCUMENTS

| | | | |
|---|---|---|---|
| 4,052,461 | 10/1977 | Tinker et al. | 568/454 |
| 4,200,765 | 10/1980 | Goetz | 568/462 |
| 4,291,179 | 9/1981 | Goetz et al. | 568/462 |

FOREIGN PATENT DOCUMENTS 7407544 12/1974 Netherlands ..................... 568/458

Primary Examiner—Werren B. Lone
Attorney, Agent, or Firm—Joseph D. Kennedy; James W. Williams, Jr.

[57] ABSTRACT

Formaldehyde is reacted with hydrogen and carbon monoxide in the presence of certain rhodium catalysts and basic organic amine compositions which promote the formation of glycol aldehyde.

11 Claims, No Drawings

HYDROFORMYLATION OF FORMALDEHYDE WITH RHODIUM CATALYSTS

This invention relates to improvements in the production of glycol aldehyde by the reaction of formaldehyde, carbon monoxide and hydrogen in a solvent system in the presence of rhodium catalysts having certain ligands associated therewith and basic organic amine compositions.

BACKGROUND OF THE INVENTION

Glycol aldehyde is a valuable intermediate useful in the synthesis of other organic compounds, and can be converted, for example, to ethylene glycol by hydrogenation. Processes for the production of glycol aldehyde by the reaction of formaldehyde with carbon monoxide and hydrogen in the presence of certain rhodium catalysts are described in the co-pending application of Alwyn Spencer, Ser. No. 256,183 filed Apr. 21, 1981, assigned to the same assignee as the present application, and in U.S. Pat. No. 4,200,765, issued to Richard W. Goetz on Apr. 29, 1980. The present invention is an improvement over the above mentioned processes in that the present applicants have found that the yields of glycol aldehyde can be improved and the reaction rate can be increased if the reaction is catalyzed with rhodium catalysts having certain ligands associated therewith and is carried out in the presence of basic organic amine compositions. Moreover, by operating within the scope of the process of this invention, it is also possible to achive stable catalyst compositions which can be reused in the production of glycol aldehyde.

It should be noted that the aforementioned patent describes that amines have a deleterious effect on the yield of glycol aldehyde from formaldehyde, carbon monoxide and hydrogen. However, this conclusion was reached because the rhodium catalyst employed by the patentee in conjunction with basic amines actually gave an adverse effect. The present applicants have found that basic organic amines actually improve the process if employed in conjunction with certain rhodium catalysts as more fully described hereinafter.

SUMMARY OF THE INVENTION

The improved process of the present invention is carried out by reacting formaldehyde, carbon monoxide and hydrogen (under temperature and pressure conditions conducive to the formation of glycol aldehyde) in the presence of (1) a rhodium catalyst having a modifying ligand in which at least one component is a tertiary organo phosphorous moiety or a tertiary organo arsenic moiety and (2) a basic organic amine composition having a pKa value in excess of 1.0, preferably a tertiary amine, to form glycolaldehyde. The reaction is carried out in a solvent which is, preferably, a solvent for the rhodium catalyst employed.

The rhodium catalysts used herein are comprised of a rhodium component in association with a modifying ligand having at least one of the components mentioned above and described in detail in U.S. Pat. No. 4,052,461, issued to Harold B. Tinker and Donald E. Morris on Oct. 4, 1977 and the aforementioned U.S. patent application Ser. No. 256,183, both of which are hereby incorporated by reference in the present description. Generally, the rhodium component of such catalysts is considered to be present in the form of a coordination compound. In addition to the rhodium component and modifying ligand, such coordination compound can include carbon monoxide (CO)ligands, hydride (H) ligands, halide or pseudo-halide components, or various other ligands. The term "coordination compound" as used herein means a compound or complex formed by a combination of one or more electronically rich molecules or atoms capable of independent existence with one or more electronically poor molecules or atoms each of which may also be capable of independent existence. The rhodium may be complexed with from 3 to 6 or so ligands of which at least one is a modifying ligand as above mentioned, and can be in a form usually considered as neutral or essentially non-valent in common catalyst systems, or in cationic form as described in the aforesaid U.S. Pat. No. 4,052,461. The catalyst can be supplied to the reactants in active form or in the form of various catalyst precursors and the catalyst also may undergo changes in the course of the reaction, or from the effect of the reaction conditions.

The term "modifying ligand" used throughout this specification (as well as in aforesaid U.S. Pat. No. 4,052,461) means a tertiary organo phosphorus compound or a tertiary organo arsenic compound. Such compound is either coordinated to the rhodium atom to form the coordination compound or complex, or is present as the free compound, i.e. uncoordinated or uncomplexed or in both forms, in the reaction solution containing the rhodium coordination complex. In the free compound state such compound has the potential to become coordinated to the rhodium atom via a ligand exchange reaction with a different ligand already coordinated to the rhodium atom.

Suitable organo phosphorus and organo arsenic modifying ligands which may comprise part of the ionic or neutral rhodium coordination compound used in this invention are those containing trivalent phosphorus and/or arsenic atoms, and are referred to in this specification as phosphines or arsines.

In this group of suitable modifying ligands, the individual phosphorus or arsenic atoms have one available or unshared pair of electrons. An organic derivative of the phosphorus arsenic with the foregoing electronic configuration is, therefore a suitable ligand for the rhodium containing catalyst employed in this invention. Organic radicals of any size and composition may be bonded to the phosphorous or arsenic, and the radicals are preferably selected from the group consisting of aryl and alkyl groups. The more preferred ligands are those consisting of at least one but preferably two or three aryl groups as the organic moieties. For example, preferred modifying ligands are illustrated by the following structural formulae $MR_3$ where M is P or As, and R is e.g. phenyl ($C_6H_5-$), or tolyl ($CH_3$)($C_6H_4-$), xylyl ($CH_3C_6H_3CH_3$), e.g. $P(C_6H_5)_3$, $As(C_6H_5)_3$, $P[CH_3(C_6H_4)]_3$.

The more preferred group of modifying ligands includes the triaryl phosphines or triaryl arsines. The preferred component, the phenyl radical.

The modifying ligands, and, if desired, other ligands, satisfy the coordination number of the central rhodium atom, and thus form a rhodium-containing complex. The term coordination compound or coordination complex means a compound or complex formed by combination of one or more electronically rich molecules or atoms, e.g, triphenylphosphine, carbon monoxide, 1,5-cyclooctadiene, (herein referred to as COD), with one or more electronically poor molecules or atoms, e.g. rhodium.

The rhodium complexes used in the present invention are ionic or neutral compounds, with the ionic ones having a non-complexing anionic moiety and the neutral ones containing halide, pseudo halide or hydride moiety. These have the general formula $RhL_{x+}An$. In this formula, in the case of the ionic ones, rhodium moiety is $RhL_x$ and the non-coordinating anionic moiety $An-$ is exemplified by $BF_4-$, $ClO_4$, $PF_6-$, $NO_3-$, and $SiF_6{}^{2-}$, and in the neutral ones An is halide, pseudo halide or hydride.

In the above formulae L is a ligand, (either the same or different ligands as described herein) and x varies from 2 to 5. The ligand L may or may not be a modifying ligand. For example, in the case where $[Rh(Ph_3P)_3]+$ is employed as the rhodium-containing cation $Ph_3P$ is the ligand L and it is also a modifying ligand. In the case where $[Rh(COD)(Ph_3P)_2]+$ is employed as the rhodium-containing cation $Ph_3P$ and COD are the ligands L, but only $Ph_3P$ is a modifying ligand. Finally, in the case where $[Rh(COD)_2]+$ is employed as the rhodium-containing cation, COD is the ligand L, and at least two moles or a modifying ligand such as $Ph_3P$ is furnished to the reaction solution per mole of rhodium to obtain the catalyst of the present invention. In cases where the ligand L is not a modifying ligand, then it is a ligand displaceable by carbon monoxide under reaction conditions, e.g. COD. Examples of the ligand L include:

- mono-enes of 2 to 12 carbon atoms,
- dienes of 4 to 12 carbon atoms,
- trienes of 6 to 16 carbon atoms,
- alkynes of 2 to 12 carbon atoms,
- ketones of 3 to 12 carbon atoms,
- nitriles of 2 to 12 carbon atoms,
- N-alkylamines of 2 to 12 carbon atoms,
- N-N-dialkylamides of 3 to 12 carbon atoms,
- sulfoxides of 2 to 12 carbon atoms,
- tertiary organo phosphorus compounds of 3 to 90 carbon atoms,
- tertiary organo arsenic compounds of 3 to 90 carbon atoms,
- tertiary organo antimony compounds of 3 to 90 carbon atoms.
- carbon monoxide, and combinations thereof.

The ionic or neutral rhodium compounds described above are utilized in the present invention as a means of introducing rhodium into the reaction solution and are sometimes referred to as catalyst precursors. Other forms of rhodium may be used to form the rhodium catalyst, for example, rhodium metal or rhodium metal on carbon or rhodium halide may be introduced into the system to form the rhodium catalyst.

Although rhodium catalysts having not more than one modifying ligand associated with one rhodium atom are useful in the practice of this invention, it is preferred to employ an amount of phosphine or arsine compound in excess of one modifying ligand for each one rhodium atom. The reason for this preference is that a higher amount of modifying ligand has been found to provide a more stable and therefore reusable catalyst system than with lower amounts of modifying ligand. At the same time, the reaction rates and selectivity of rhodium catalysts containing such higher amounts of modifying ligand are quite satisfactory when using a basic amine composition in the process, whereas the reaction rates decrease considerably in the absence of basic organic amine compositions. Amounts of phosphines or arsenine compounds as high as 200 mls per rhodium atom in the catalyst complex have been used successfully in the present process, although some reduction in reaction rate and selectivity is experienced with such larger amounts.

The basic organic amine compositions employed in the hydroformylation process of this invention can be any amine compound, or combinations of compounds, which are basic in relation to any of the reactants or solvents employed in the process. The term "basic" is used herein to mean that the amine composition has a pH in water solution which is higher than the pH of such reactants or solvents.

As noted previously herein, the basic organic amines used in the present process have a pKa of at least 1.0, which incidentally contrasts with the lower pKa values of N,N-disubstituted amides which usually have a pKa below 0.7. While amines having a pKa of at least 1.0 can be used, it is preferred to use amines having a pKa in the range of about 4.0 to about 12.5 since such amines generally provide improved reaction rates.

As examples of one class of basic organic amine compositions which can be used are basic amines having the structural formula

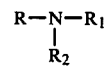

where R, $R_1$ and $R_2$ are the same or dissimilar organo radicals such as alkyl, aryl, alkaryl or aralkyl radicals or radicals of the foregoing kind which have been substituted with one or more substituents such as halide, hydroxyl, amine or other groups. Illustrative of such tertiary amines are trimethyl amine, triethyl amine, tributyl amine, dimethyl ethyl amine, triphenyl amine, triethanolamine, tri(chloromethyl)amine, 1,8-bis(dimethylamino)-naphthalene, pyridine, polyvinylpyridine-styrene copolymers and the like.

It will be understood that the above listed compounds are merely illustrative and not limiting of the tertiary amine compounds, or combinations thereof, which are useful in the processes of this invention.

As further examples of basic organic amine compositions which can be employed are basic secondary amines having the structural formula

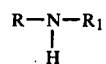

wherein R and $R_1$ have the same significance as stated above. Illustrative of such secondary amines are dimethyl amine, diethylamine, dibutylamine, diphenylamine, diethanolamine, dichloromethyl amine and the like. It will be understood that the above listed secondary amines are merely illustrative and not limiting of the secondary amine compounds, or combinations thereof, which are useful in the processes of this invention. Also, it is possible to use such secondary amines, or any of them, in combination with tertiary amines if desired.

As further examples of basic organic amine compositions which can be employed are basic primary amines having the structural formula:

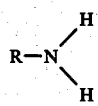

where R has the same significance as stated above. Illustrative of such primary amines are monomethyl amine, monoethyl amine, monobutylamine, monophenyl amine, mono (chloromethyl) amine, monoethanol amine and the like. It will be understood that the above listed compounds are merely illustrative and not limiting of the primary amines, or combinations thereof, which are useful in the processes of this invention. Moreover, it is possible to use such primary amines or any of them in combination with the hereinbefore described tertiary and/or secondary amines.

The applicants have found that by using the basic organic amine compositions in the hydroformylation processes described herein it is possible to obtain a number of important benefits not heretofore attained in such processes or prior art. One of these benefits—as already noted—is that the reaction rate of formaldehyde, carbon monoxide and hydrogen to produce the desired glycol aldehyde can be increased. Another benefit is that by increasing the modifying ligand to rhodium ratio in the catalyst it is possible to achieve a stable and hence reusable catalyst system without detrimental loss of reaction rate as would otherwise occur.

A third benefit is that almost any solvent system for the hydroformylation process can be used without materially affecting in an adverse manner the yield of glycol aldehyde from the starting formaldehyde material. The prior art has stressed the desirability of employing polar solvents and particularly substituted amide solvents which are distinguished by the absence of hydrogen atoms linked to the amide nitrogen atom. Thus, both U.S. Pat. No. 4,200,765 and patent application Ser. No. 256,183, previously referred to herein, stress the desirability, from the standpoint of attaining good yields, of using such substituted amide solvents compared to other solvents. However, the process of this invention can be practised advantageously in any solvent which does not enter into the hydroformylation reaction. Suitable solvents which may be used include the following: (1) nitriles, such as acetonitrile, benzonitrile, propionitrile and the like; (2) cyclic ethers such as tetrahydrofuran, tetrahydropyran, dioxane and the like; (3) ethers such as diethyl ether, alkyl ethers of alkylene glycols and polyalkylene glycols, for example, methyl ethers of ethylene glycol, methyl ethers of propylene glycol and methyl ether, of di-, tri- and tetraethylene glycols. For example, tetraethylene glycol dimethyl ether (tetraglyme) and the like, (4) ketones, such as acetone, methyl isobutyl ketone, cyclohexanone and the like; (5) esters such as ethyl propionate, methyl laurate, ethyl acetate and the like. Another variety of suitable solvents is exemplified by N-substituted amides in which each hydrogen of the amido group is substituted by an organo group, usually a hydrocarbyl group such as an alkyl group as, for example, lower alkyl groups such as methyl, ethyl, propyl, butyl, hexyl, and the like. These amides are generally the amides of lower carboxylic acids, such as formic, acetic, propionic, hexenoic acids and the like. Specific amides of the above type which can be used include N,N-dimethyl formamide, N,N-di-n-butyl formamide, N,N-di-isopentyl formamide, N,N-dimethyl acetamide, N,N-diethyl acetamide, N-methyl-N-benzyl formamide and the like. Other amides may also be used as solvents such as 1-methyl-pyrolidine-2-one, N-methyl piperidone, 1-benzyl pyrrolidine-2-one and the like.

As examples of other polar solvents which may be used are sulfoxides such as methyl sulfoxide, ethyl sulfoxide and the like, sulfones such as

in which R is methyl, ethyl or the like; phosphine oxides such as trimethyl phosphine oxide, triethyl phosphine oxide and the like; lactones such as propanolide, butanolide and the like.

The amines herein can be used in widely varying amounts such as from less than 0.5 to more than 50 moles per rhodium atom, with a tendency to use less of an amine as its basic character increases. With many of the amines, such as triethylamine, a range of about 1 to about 5 mols amine per rhodium atom in the rhodium catalyst is preferred.

In most instances, mixed solvents, that is, a homogeneous solution of two or more miscible solvents, may also be used. The above enumeration of solvents is illustrative and not intended to be limited.

The preferred solvents for use in the hydroformylation processes of this invention are acetone, acetonitrile, the N,N-alkyl substituted formamides and acetamides and tetraglyme.

The hydroformylation processes of this invention are generally carried out at somewhat elevated pressures and temperatures, but in most instances relatively mild temperatures and pressures are not only desirable, but preferable. Generally higher pressures provide the best reaction rates and selectivity, but pressures not in excess of 6000 psi may be used if optimum reaction rates and selectivity are not required. The processes are temperature dependent and it is generally desirable to use moderate temperatures of the order of 70° C. up to 150° C., and preferably from 90° C. up to 120° C.

The pressures referred to above are usually attained by the quantities of carbon monoxide and hydrogen charged to the reaction zone or system, which is normally provided by an autoclave or other pressure resistant vessel. While the CO and $H_2$ react in a 1:1 mole ratio in the hydroformylation process, it is not necessary to have them present in such ratio for the reaction. The CO and H may conveniently be used in a mole ratio of about 1:1 as available in synthesis gas, but can also be employed in widely varying ranges, such as $CO:H_2$ mole ratios varying from about 10:90 to 90:10. Usually, however, it is desirable to employ $CO:H_2$ mole ratios in the range of about 4:1 to about 1:2, and to avoid large excesses of hydrogen thereby suppressing methanol production.

The formaldehyde employed in the processes can be utilized in any form which will generate formaldehyde under the reaction conditions. A preferred form of formaldehyde is paraformaldehyde.

The amount of catalyst employed in the hydroformylation processes herein does not appear to be critical and can vary considerably without adversely affecting the course of the reaction. In any event, the amount of catalyst used should be sufficient to catalyze the hydroformylation of formaldehyde with carbon monoxide and hydrogen to form glycol aldehyde, and, preferably, should be sufficient to achieve a reasonably practical reaction rate. Generally, the rhodium catalysts are used in amounts sufficient to provide at least about 0.001 gram atoms of rhodium, and up to about 0.09 gram atoms of rhodium, per liter of the reaction medium. The preferred amounts for most purposes are in the range of from about 0.003 to about 0.03 gram atoms per liter.

The following specific examples are intended to illustrate the processes of this invention, but not to limit the scope thereof. In these examples the term "m mole" is intended to mean milli moles.

EXAMPLE 1

A 300 ml. stainless steel autoclave, equipped with a Magnedrive mechanical stirrer, was charged with 0.345 g. (0.5 millimole) of $RhCl(CO)(PPh_3)_2$, 6.2 g. of paraformaldehyde (97% pure, 0.2 mole), 0.2 ml (1.4 millimole) triethylamine and 100 ml tetraglyme(tetraethylene glycol dimethyl ether). The autoclave was heated to 110° C. under 4000 psig of $CO:H_2(1:1)$. After 30 minutes under these conditions, the autoclave was cooled to room temperature and the gas vented. Gas chromatographyc analysis of the resulting solution showed 0.36 g. of formaldehyde (6% of the amount charged) left in solution. Also present were glycolaldehyde (8.8 g., 78% selectivity) and methanol (0.3 g., 5% selectivity). The balance of products were found to be higher boiling materials.

EXAMPLE 2

Similar to example 1, except that the ingredients charged to the autoclave were 0.345 g. (0.5 mmole) of $RhCl(CO)(PPh_3)_2$, 0.364 g. (2.4 mmole) triethanolamine, 81.4 g. tetraglyme and 6.2 g. paraformaldehyde (97% pure, 0.2 mole). The products after 30 minutes of reaction were 5.04 of glycolaldehyde (64% selectivity) and 0.33 g. methanol (9.5% selectivity). 2.04 g. formaldehyde (34% of the amount charged) was left unreacted. The remaining materials were high boilers.

EXAMPLE 3

Similar to example 2, except that the reaction time was 1.5 hours. The products were glycolaldehyde (6.6 g. 63% selectivity) and methanol (0.96 g., 18% selectivity). The amount of unreacted formaldehyde was 0.78 g. (13% of the amount charged).

EXAMPLE 4

Similar to example 1, except that the materials charged to the autoclave were 0.34 g. (0.5 mmole) of $RhCl(CO)(PPh_3)_2$, 0.247 g. (1.66 mmole) triethanolamine, 6.2 g. paraformaldehyde (97% pure, 0.2 mole) and 73.5 g. acetone. Products identified after 1.5 hours of reaction were glycolaldehyde (6.5 g, 68% selectivity) and methanol (1.08 g. 23% selectivity). Unreacted formaldehyde amounted to 1.26 g. (21% of the original charge) and the remaining products were high boilers.

EXAMPLE 5

Similar to example 1, except that the materials charged to the autoclave were 0.34 g. (0.5 mmole) of $[Rh(1,5-COD)(PPh_3)((CH_3)_2CO)]\ PF_6$, 0.27 g. (1.3 mmole) of 1,8-bis(dimethylamino)naphthalene, 6.2 g. paraformaldehyde (97% pure, 0.2 mole) and 100 ml acetonitrile. After 1.5 hours of reaction the products were found to be glycoaldehyde (6.12 g. 62% selectivity), methanol (1.53 g. 29% selectivity) and 1.06 g unreacted formaldehyde (17.7% of the original charge). 1,5-COD, referred to above, is 1,5 cyclooctadiene.

EXAMPLE 6

The autoclave used in Example 1 was charged with 0.345 g. (0.5 mmole) $RhCl(CO)(PPh_3)_2$, 6.2 g. polyvinylpyridinestyrene copolymer (30% styrene), 3.1 g. paraformaldehyde (97% pure, 0.1 mole) and 100 ml tetraglyme and reacted under the conditions of example 1. After 1.5 hours the products were glycolaldehyde (4.88 g., 84% selectivity), and methanol (0.13 g., 4.6% selectivity) with 0.39 g. unreacted formaldehyde remaining (13% of the amount charged).

EXAMPLE 7

Similar to example 1 except that the reactants were 0.395 g. (0.5 mmole) of $[Rh(C_5Me_5)(DMA)_3](PF_6)_2$, 0.363 g. (1.4 mmole) $PPh_3$, 0.3 ml (2.2 mmole) triethylamine, 6.2 g paraformaldehyde (97% pure, 0.2 mole) and 75.4 g. acetone. After 30 minutes of reaction the products were found to be glycolaldehyde (9.7 g., 86% selectivity) and methanol (0.62 g., 10.3% selectivity) with 0.35 g. unreacted formaldehyde (6% of the amount charged). $C_5Me_5$ and DMA, referred to above are pentamethyl cyclopentadiene and dimethyl acetamide respectively.

EXAMPLE 8

Similar to example 1, except that the reaction pressure was 1400 psig and the reactants charged the autoclave were 0.33 g. (0.5 mmole) of $[Rh(NBD)(PPh_3)(DMA)]PF_6$, 5 g. (20 mmole) of 1,8-bis(dimethylamino)naphthalene, 3.1 g. paraformaldehyde (97% pure, 0.1 mole) and 100 ml acetonitrile. After 1 hour of reaction the products were found to be glycolaldehyde (2.7 g., 56% selectivity) and methanol (0.76 g. 28% selectivity) with 0.6 g. unreacted formaldehyde (20% of the original charge). NBD and DMA, referred to above, are norbornadiene and N,N-dimethyl acetamide, respectively.

EXAMPLE 9

The autoclave was charged with $[Rh(1,5-COD)(DMA)(PPh_3)]BF_4$ (0.31 g., 0.5 mmole), pyridine (0.06 g. 0.7 mmole), acetone (100 ml) and paraformaldehyde (3.1 g., 97% purity, 0.1 mole). The reaction mixture was heated, with stirring, to 110° C. under 2500 psig of $CO:H_2(1:1)$. After 2 hours the autoclave was cooled to room temperature and the gases vented. Gas chromatographic analysis showed the products to be formaldehyde (0.51 g., 17% of the amount charged), glycolaldehyde (3.72 g., 74.7% selectivity) and methanol (0.16 g., 6.4% selectivity). 1,5-COD and DMA, referred to above, are 1,5 cyclooctadiene and N,N-dimethyl acetamide, respectively.

EXAMPLE 10

The autoclave was charged with 0.41 g. (0.5 mmole) of $[Rh(1,5-COD)(PPh_3)_2]BF_4$, 0.15 g. (2 mmole) diethylamine, 6.2 g. paraformaldehyde (97% pure, 0.2 mole) and 100 ml acetone. The mixture was heated to 110° C. and pressured to 3500 psig with $CO:H_2(1:1)$. After ½ hour the reactor was cooled and the contents analyzed. The products were found to be glycolaldehyde (6.268 g., 57% selectivity) and methanol (0.486 g., 8.2% selectivity) with 0.498 g. unreacted formaldehyde (8.3% of the original charge). 1,5-COD, referred to above, is 1,5 cyclooctadiene.

EXAMPLE 11

Similar to example 10, except that 0.17 g. (2 mmole) of piperidine replaced the diethylamine. After ½ hour of reaction, the products were glycolaldehyde (7.78 g., 76.7% selectivity) and methanol (0.68 g., 12.6% selectivity) with 0.93 g. unreacted formaldehyde (15.4% of the original charged).

EXAMPLE 12

Similar to example 10, except that 0.12 g. 2 mmole) of ethylenediamine replaced the diethylamine. After 30 minutes of reaction, the products were glycolaldehyde (8.064 g., 74.3% selectivity) and methanol (0.541 g., 9.4% selectivity) with 0.574 g. unreacted formaldehyde (9.6% of the amount charged).

EXAMPLE 13

The procedure of example 1 was repeated except that the materials charged to the autoclave were 0.345 g. (0.5 mmole) RhCl(CO)(PPh$_3$)$_2$, 0.262 g. (1 mmole) PPh$_3$, 0.2 ml (1.4 mmole) triethylamine, 6.2 g. paraformaldehyde (97% pure, 0.2 mole) and 100 ml N,N-dibutylformamide. After 30 minutes of reaction the formaldehyde conversion was 86% with selectivities of 91% to glycolaldehyde and 2% to methanol.

EXAMPLE 14

The procedure of example 1 was repeated except that the reagents were 0.41 g. (0.5 mmole) [Rh(NBD)(PPh$_3$)$_2$]BF$_4$, 4 g. (15.3 mmole) triphenylphosphine, 0.2 g. (2.1 mmole) triethylamine, 6.2 g. paraformaldehyde (97% pure, 0.2 mole) and 100 ml N,N-dimethylacetamide and the pressure was 2500 psig. After 30 minutes of reaction the formaldehyde conversion was 91% with selectivities of 67% to glycolaldehyde and 3% to methanol. NBD, referred to above is norbornadiene.

EXAMPLE 15

The procedure of example 14 was repeated except that the catalyst precursor was RhH(CO)(PPh$_3$)$_3$ (0.459 g., 0.5 mmole). After 30 minutes of reaction, the formaldehyde conversion was 95% with selectivities of 71% glycolaldehyde and 2% to methanol.

EXAMPLE 16

The procedure of example 14 was repeated except that the catalyst precursor was RhCl(CO)(PPh$_3$)$_2$ (0.345 g., 0.5 mmole) and the solvent was 100 ml of N,N-dibutylformamide. After 30 minutes of reaction, the formaldehyde conversion was 92% with selectivities of 68% to glycolaldehyde and 5% to methanol.

EXAMPLE 17

The procedure of example 14 was repeated, except that the catalyst precursor was RhCl(CO)(PPh$_3$)$_2$ (0.345 g., 0.5 mmole) and the amount of triethylamine was 0.08 g. (0.84 mmole). After 30 minutes of reaction, the formaldehyde conversion was 43%, while the selectivities to glycolaldehyde and methanol were 86% and 5%, respectively.

EXAMPLE 18

Similar to example 14, except that the reactants were 0.345 g. (0.5 mmole) RhCl(CO)(PPh$_3$)$_2$, 4 g. (15.3 mmole) PPh$_3$, 0.18 g. (1.9 mmole) triethylamine, 12.4 g. paraformaldehyde (97% pure, 0.4 mole) and 100 ml N,N-dimethylacetamide. After 30 minutes of reaction, the formaldehyde conversion was 88% while the selectivites to glycolaldehyde and methanol were 69% and 5%, respectively.

EXAMPLE 19

The procedure of example 16 was repeated, except that the pressure was 1000 psig. After 30 minutes of reaction the formaldehyde conversion was 76% with selectivities to glycolaldehyde and methanol of 63% and 9%, respectively.

EXAMPLE 20

Similar to example 16, except that the reaction temperature was 90° C. After 30 minutes of reaction the formaldehyde conversion was 66% with selectivities of 79% to glycolaldehyde and 5% to methanol.

EXAMPLE 21

The procedure of example 16 was repeated, except that the amount of triphenylphosphine was increased to 20 g. (76.3 mmole) and the solvent was 100 ml of hexamethylphosphonamide. After 30 minutes of reaction the formaldehyde conversion was 65% with selectivities of 80% to glycolaldehyde and 8% to methanol.

EXAMPLE 22

The procedure of example 14 was repeated, except that the catalyst precursor was 0.123 g. (0.5 mmole Rh) of [Rh(1,5-COD)Cl]$_2$ and the triphenylphosphine was replaced with 0.5 g. (1.1 mmole) of Ph$_2$P(CH$_2$)$_6$PPh$_2$. After 30 minutes of reaction, the formaldehyde conversion was 79%. Selectivities to glycolaldehyde and methanol were 73% and 8%, respectively. 1,5-COD, referred to above, is 1,5-cyclo octadiene.

EXAMPLE 23

Similar to example 22, except that the phosphine ligand was replaced by 31 g. (101 mmole) of triphenylarsine. After 30 minutes of reaction, the formaldehyde conversion was 54%, with a selectivity of 63% to glycolaldehyde. No significant amount of methanol was found.

EXAMPLE 24

(This example indicates that without phosphine or arsine ligands, the catalyst system is not efficient for the formaldehyde hydroformylation).

The procedure of example 14 was repeated except that the reactants were [Rh(1,5-COD)Cl]$_2$ (0.122 g., 0.5 mmol Rh), 0.2 g. triethylamine (2.1 mmole), 6.2 g. paraformaldehyde (97% pure, 0.2 mol) and 1000 ml tetraglyme solvent. After 1.5 hours of reaction the formaldehyde conversion was 76% with selectivity of 5% to glycolaldehyde and 25% to methanol.

EXAMPLE 25

A 300 ml stainless steel autoclave equipped with a magnedrive mechanical stirrer was charged with 2.2 g of 5% Rh on carbon power (1 mmole Rh), 8.1 g. PPh$_3$ (31 mmole), 0.3 g. triethylamine (3 mmole), 6.2 g. paraformaldehyde (97% pure, 0.2 mole) and 100 ml N,N-dimethylacetamide solvent. The content was stirred at 110° C. under 2500 psig 1:1 CO:H$_2$ for 1 hour. Gas chromatography analysis of the product indicated 98% conversion of formaldehyde with 55% selectivity for glycolaldehyde and 4% selectivity for methanol.

EXAMPLE 26

A 300 ml stainless steel autoclave equipped with a magnedrive mechanical stirrer was charged with 0.345 g. RhI(CO)(PPh$_3$)$_2$ (0.5 mmole), 1.05 g. PPh$_3$ (4 mmole), 0.19 g. triethylamine (1.9 mmole), 6.2 g. paraformaldehyde (97% pure, 0.2 mole), 3.2 g. H$_2$O and 100 ml N,N-dibutylformamide. The autoclave was stirred under 4000 psig of CO:H$_2$ (1:1). After 30 minutes of reaction, the autoclave was cooled to room temperature and the gas was vented. Gas chromatography analysis of the products indicated 98% conversion of formaldehyde with 57% selectivity for glycolaldehyde and 7% selectivity for methanol. The balance of products were higher boiling materials. The results indicate that the catalyst system can tolerate some water.

EXAMPLE 27

The organic products from example 26 were extracted with 50 ml water three times. (Gas chromatographic analysis of the remaining solution indicated no glycolaldehyde or methanol left.) The volume of the remaining solution which contained the catalyst and the phosphine ligands was adjusted to 100 ml by adding a small amount of N,N-dibutylformamide solvent. This catalyst solution and 6.2 g. paraformaldehyde, 0.19 g. triethylamine, 3.2 g. water and 0.5 g. PPh$_3$ were charged to the autoclave. (The PPh$_3$ was added because some PPh$_3$ was oxidized during the extraction procedure which was performed in air.) The autoclave was heated to 110° C. and the content was stirred under 4000 psig CO:H$_2$ (1:1) for 30 minutes. Gas chromatographic analysis of the products indicated 97% conversion of formaldehyde with 54% selectivity for glycolaldehyde and 5% selectivity for methanol. The balance of products were higher boiling materials.

Within experimental error these results (examples 26 and 27) indicate that the catalyst can be recycled without loss of activity and selectivity.

What is claimed is:

1. A process for the production of glycol aldehyde which comprises reacting carbon monoxide, hydrogen and formaldehyde in a solvent system and in the presence of (1) an amount of a rhodium catalyst sufficient to catalyze the formation of glycol aldehyde and wherein the rhodium catalyst has at least one modifying ligand associated with one rhodium atom and said ligand is a tertiary organo phosphorus moiety or a tertiary organo arsenic moiety or combinations thereof and (2) a basic organo amine composition having a pKa of at least 1.0 serving to improve reaction rate and yield of glycolaldehyde, said process being further characterized in that it is carried out under conditions of elevated pressure not in excess of 6000 psig and elevated temperature in the range of 70° C. up to 150° C., conducive to the formation of glycol aldehyde.

2. A process as in claim 1, wherein said basic amine composition has a pH in water solution in excess of any reactant or solvent employed in said process.

3. A process as in claim 2, wherein said basic amine composition is a tertiary amine.

4. A process as in claim 3, wherein said tertiary amine is triethyl amine.

5. A process as in claim 2, wherein said basic amine composition is employed in amounts of about 1 to 5 mols of amine compound per rhodium atom in the rhodium catalyst.

6. A process for the production of glycol aldehyde which comprises reacting carbon monoxide and hydrogen in a mol ratio of about 4:1 to about 1:2 with formaldehyde in a solvent system under a pressure of about 500 to about 6000 psi and a temperature of from about 80° C. to about 120° C. in the presence of (1) an amount of a rhodium catalyst sufficient to catalyze the formation of glycol aldehyde and wherein said catalyst has an amount of organo phosphine in excess of one organo phosphine ligand associated with one rhodium atom and (2) a basic organic amine compound having a pKa of about 4.0 to about 12.5 in an amount sufficient to provide about 1 to 5 mols of said compound per rhodium atom in said catalyst.

7. A process as in claim 6, wherein the phosphine is triphenylphosphine and the amount of said phosphine present exceeds 2 mols per rhodium atom.

8. A process as in claim 6, wherein the amine compound is a tertiary amine having the structural formula

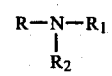

where R, R$_1$ and R$_2$ are the same or dissimilar organo radicals selected from the group consisting of alkyl, aryl, alkaryl or aralkyl radicals or one of the foregoing radicals substituted with halide, hydroxyl or amine groups.

9. The process of claim 1 in which an amide solvent is employed.

10. The process of claim 1 in which a solvent other than an amide is employed along with the other recited components.

11. The process of claim 1 in which a polar solvent is present along with the other recited components.

* * * * *